(12) United States Patent
Yuta

(10) Patent No.: US 8,473,448 B2
(45) Date of Patent: Jun. 25, 2013

(54) COMPOUND PROPERTY PREDICTION APPARATUS, PROPERTY PREDICTION METHOD, AND PROGRAM FOR IMPLEMENTING THE METHOD

(75) Inventor: Koutarou Yuta, Narashino (JP)

(73) Assignee: Fujitsu Limited, Kawasaki (JP)

( * ) Notice: Subject to any disclaimer, the term of this patent is extended or adjusted under 35 U.S.C. 154(b) by 565 days.

(21) Appl. No.: 12/707,878

(22) Filed: Feb. 18, 2010

(65) Prior Publication Data

US 2010/0145896 A1 Jun. 10, 2010

Related U.S. Application Data

(63) Continuation of application No. PCT/JP2007/066286, filed on Aug. 22, 2007.

(51) Int. Cl.
*G06F 17/00* (2006.01)
*G06N 7/04* (2006.01)

(52) U.S. Cl.
USPC ............................................................ 706/54

(58) Field of Classification Search
None
See application file for complete search history.

(56) References Cited

U.S. PATENT DOCUMENTS

| | | | | |
|---|---|---|---|---|
| 6,904,423 B1 * | 6/2005 | Nicolaou et al. | | 706/46 |
| 2002/0143476 A1 * | 10/2002 | Agrafiotis et al. | | 702/32 |
| 2004/0006559 A1 * | 1/2004 | Gange et al. | | 707/3 |
| 2004/0019432 A1 * | 1/2004 | Sawafta et al. | | 702/19 |
| 2004/0088118 A1 * | 5/2004 | Jensen et al. | | 702/30 |
| 2004/0153250 A1 * | 8/2004 | Hurst et al. | | 702/19 |

FOREIGN PATENT DOCUMENTS

| | | |
|---|---|---|
| JP | 2000-40079 | 2/2000 |
| JP | 2002-157572 | 5/2002 |
| JP | 2003-122572 | 4/2003 |
| JP | 2005-242803 | 9/2005 |
| JP | 2006-107394 | 4/2006 |
| JP | 2007-153767 | 6/2007 |
| WO | 2004/097408 A1 | 11/2004 |

OTHER PUBLICATIONS

Tatsuya Nishino et al., "Active QSAR Modeling Based on Structure Similarity", The 21$^{st}$ Annual Conference of the Japanese Society for Artificial Intelligence, 2007, pp. 1-2.
International Search Report for PCT/JP2007/066286, mailed Oct. 2, 2007.
Kazutoshi Tanabe et al.; "Neural Network Prediction of Carcinogenicity of Diverse Organi Compound"; Journal of Computer Chemistry, Japan; vol. 4, No. 3; 2005; pp. 89-100.
Japanese Office Action mailed May 15, 2012 issued in corresponding Japanese Patent Application No. 2009-528918.
Extended European Search Report for Application No. 07792876.0-1225; mailed Dec. 3, 2010.

* cited by examiner

*Primary Examiner* — Kakali Chaki
*Assistant Examiner* — Peter Coughlan
(74) *Attorney, Agent, or Firm* — Staas & Halsey LLP

(57) ABSTRACT

A compound property prediction apparatus includes a memory storing a training sample library in which a parameter value and a value for a prediction item are preregistered for each individual one of a plurality of training samples and an input device inputting data concerning an unknown sample. Also included is a processor programmed to generate a parameter of the unknown sample, calculate the degree of similarity between the unknown sample and an individual training sample, construct a sub-sample set by extracting training samples whose degree of similarity to the unknown sample is not smaller than a predetermined threshold value, construct a prediction model from the sub-sample set, and calculate the prediction value of the unknown sample based on the prediction model. If necessary, the threshold value is changed until a predetermined minimum number of training samples are included in the sub-sample set.

17 Claims, 14 Drawing Sheets

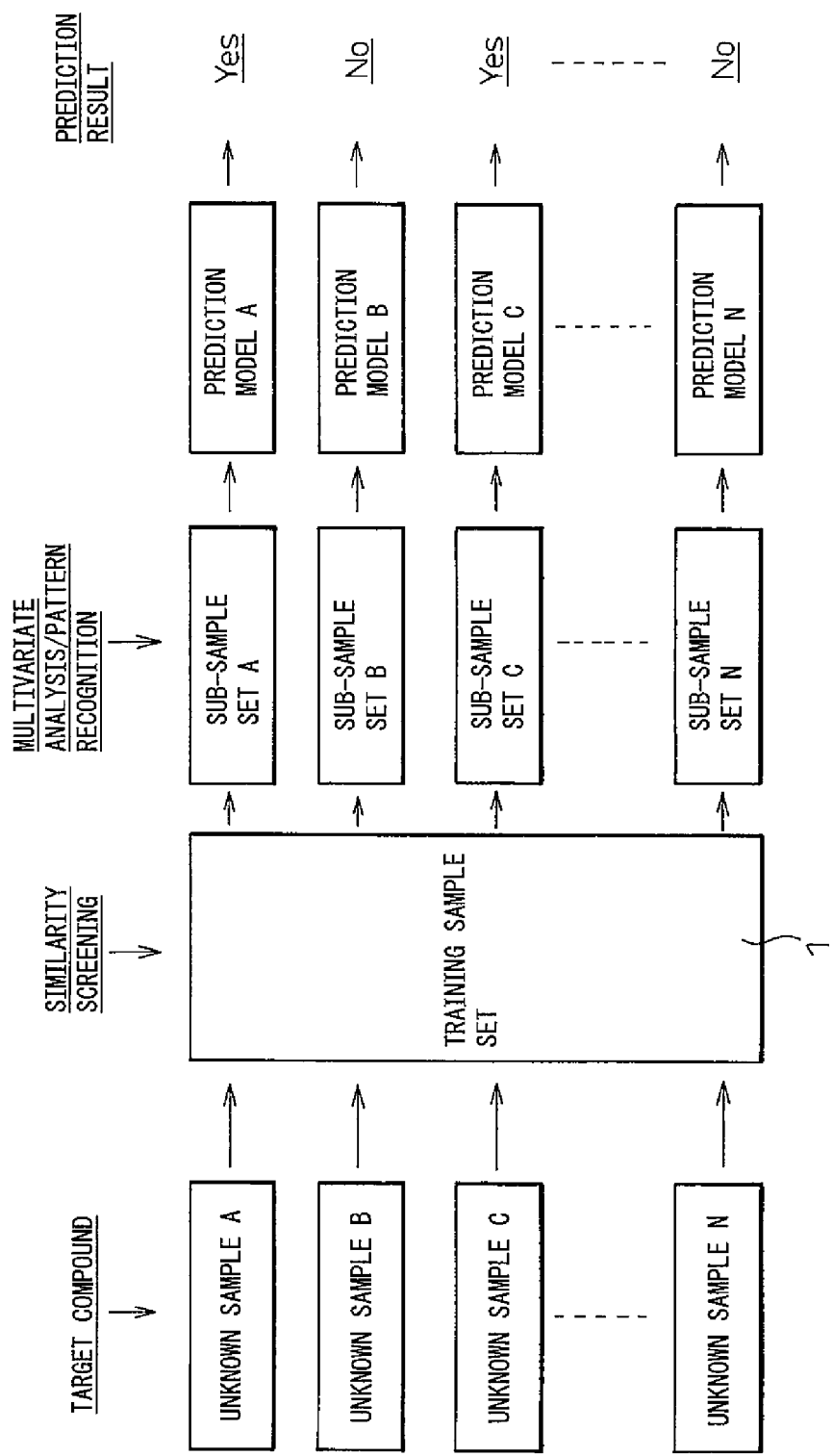

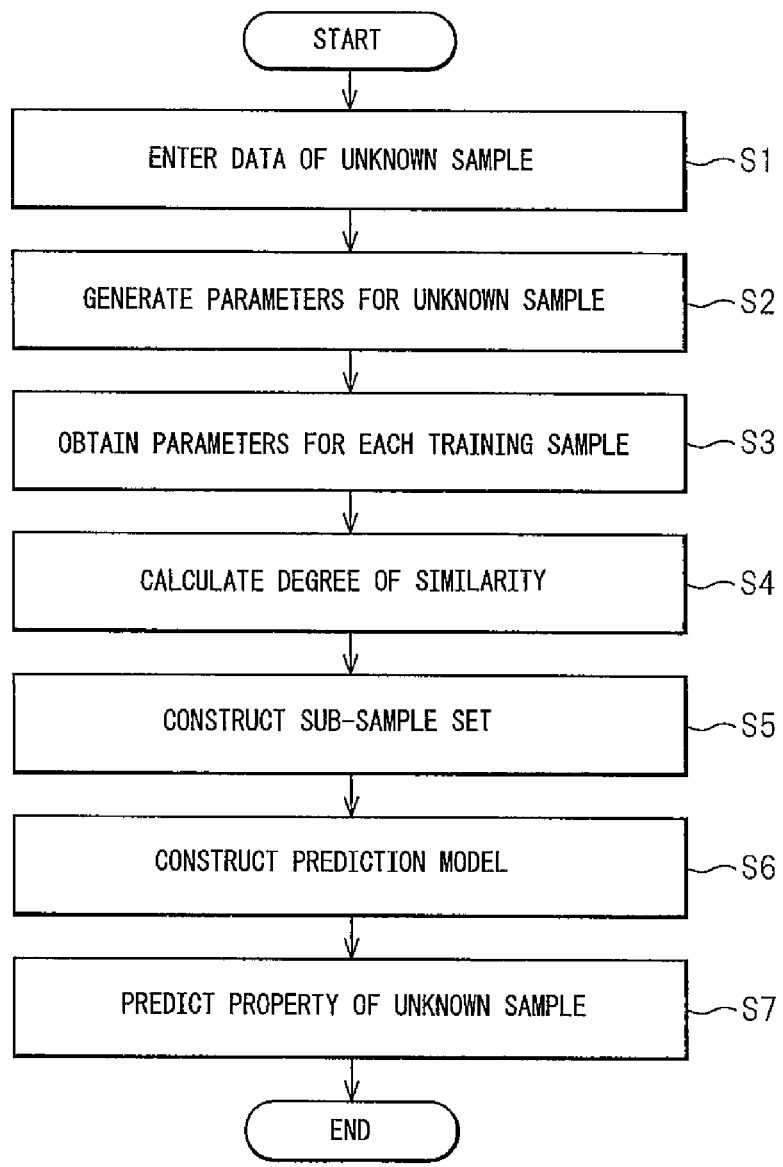

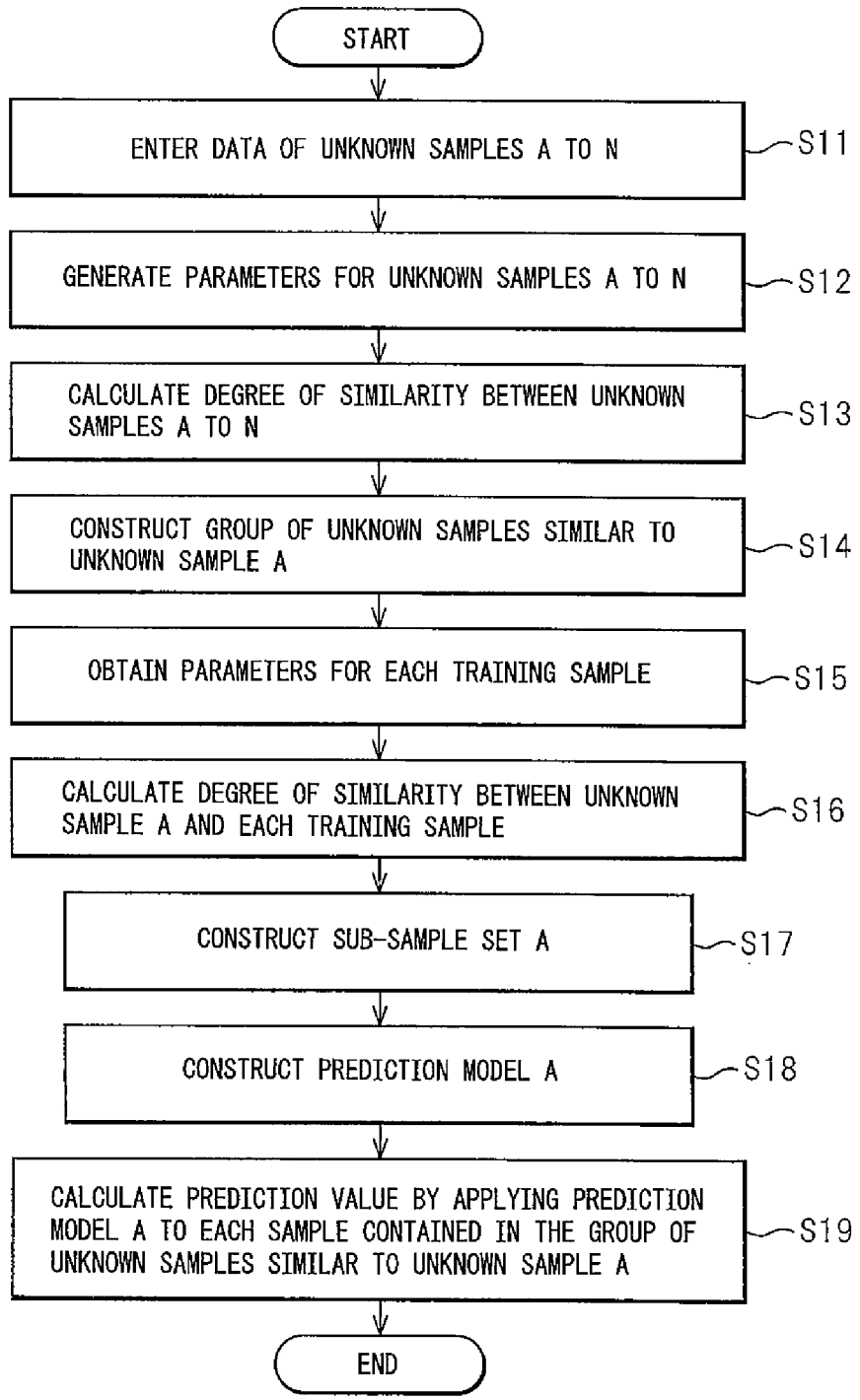

Fig.4
| ID No. | STRUCTURAL FORMULA | CAS NUMBER |
|---|---|---|
| 1 | 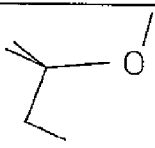 | 994-05-8 |
| 2 | 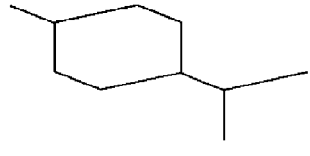 | 99-82-1 |
| 3 | 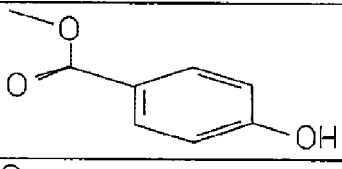 | 99-76-3 |
| 4 | 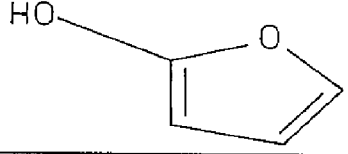 | 98-00-0 |
| 5 | 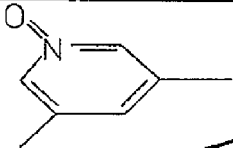 | |

Fig.5

| SAMPLE ID | FISH TOXICITY (LC50) | PARAMETERS | | | | | | | |
|---|---|---|---|---|---|---|---|---|---|
| | | NUMBER OF ATOMS | NUMBER OF CARBON ATOMS | NUMBER OF OXYGEN ATOMS | NUMBER OF NITROGEN ATOMS | NUMBER OF SULFUR ATOMS | NUMBER OF FLUORINE ATOMS | NUMBER OF CHLORINE ATOMS | NUMBER OF BROMINE ATOMS |
| 1 | 0 | 44 | 33 | 9 | 2 | 0 | 0 | 0 | 0 |
| 2 | 1 | 20 | 16 | 4 | 0 | 0 | 0 | 0 | 0 |
| 3 | 0 | 21 | 15 | 6 | 0 | 0 | 0 | 0 | 0 |
| 4 | 0 | 18 | 13 | 5 | 0 | 0 | 0 | 0 | 0 |
| 5 | 0 | 10 | 6 | 4 | 0 | 0 | 0 | 0 | 0 |
| 6 | 1 | 4 | 1 | 0 | 0 | 0 | 2 | 1 | 0 |
| 7 | 1 | 16 | 12 | 4 | 0 | 0 | 0 | 0 | 0 |
| 8 | 1 | 7 | 4 | 3 | 0 | 0 | 0 | 0 | 0 |
| 9 | 1 | 7 | 4 | 2 | 1 | 0 | 0 | 0 | 0 |
| 10 | 0 | 7 | 2 | 2 | 0 | 0 | 0 | 3 | 0 |
| 779 | 1 | 13 | 10 | 2 | 1 | 0 | 0 | 0 | 0 |

Fig. 11

| SAMPLE ID | SAFETY DATA | PREDICTION RESULTS BY PRIOR ART TECHNIQUE (AdaBoost) | PREDICTION RESULTS ACCORDING TO AN EMBODIMENT OF THE INVENTION (AdaBoost) |
|---|---|---|---|
| 169 | 0 | 0 | -- |
| 170 | 1 | 1 | 1 |
| 171 | 0 | 0 | -- |
| 172 | 0 | 0 | -- |
| 173 | 0 | 0 | -- |
| 174 | 1 | 1 | 1 |
| 175 | 1 | 0 | 0 |
| 176 | 1 | 1 | 1 |
| 177 | 1 | 1 | 1 |
| 178 | 0 | 1 | 0 |
| 179 | 0 | 0 | 0 |
| 180 | 0 | 1 | -- |
| 181 | 0 | 0 | -- |
| 182 | 0 | 0 | -- |
| 183 | 0 | 0 | -- |
| 184 | 0 | 1 | -- |
| 185 | 0 | 1 | -- |
| 186 | 1 | 1 | 1 |
| 187 | 1 | 1 | 1 |
| 188 | 1 | 1 | 1 |
| 189 | 1 | 0 | 1 |
| 190 | 1 | 1 | 1 |
| 191 | 0 | 0 | 0 |
| 192 | 0 | 1 | -- |
| 193 | 0 | 1 | -- |
| 194 | 0 | 0 | -- |

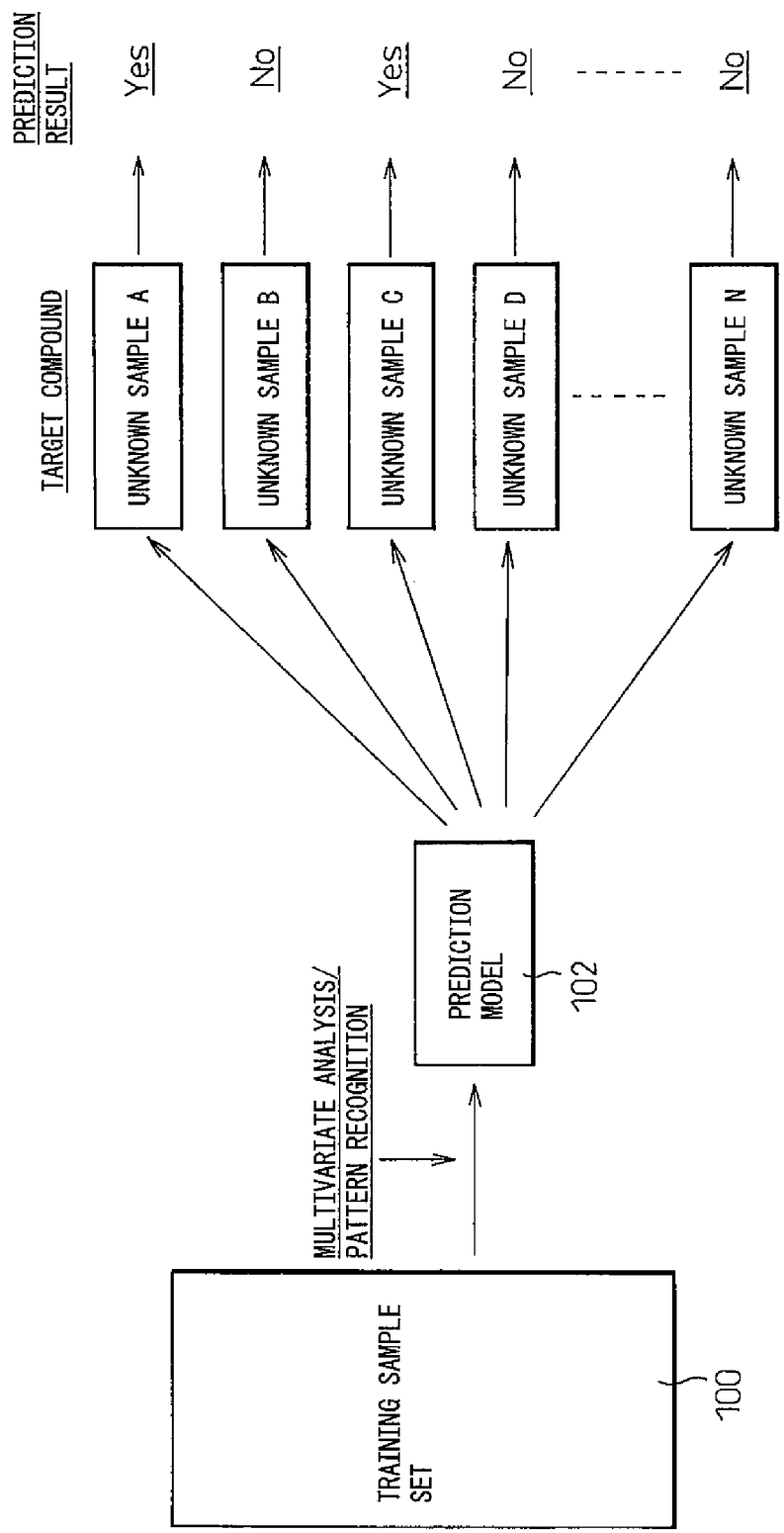

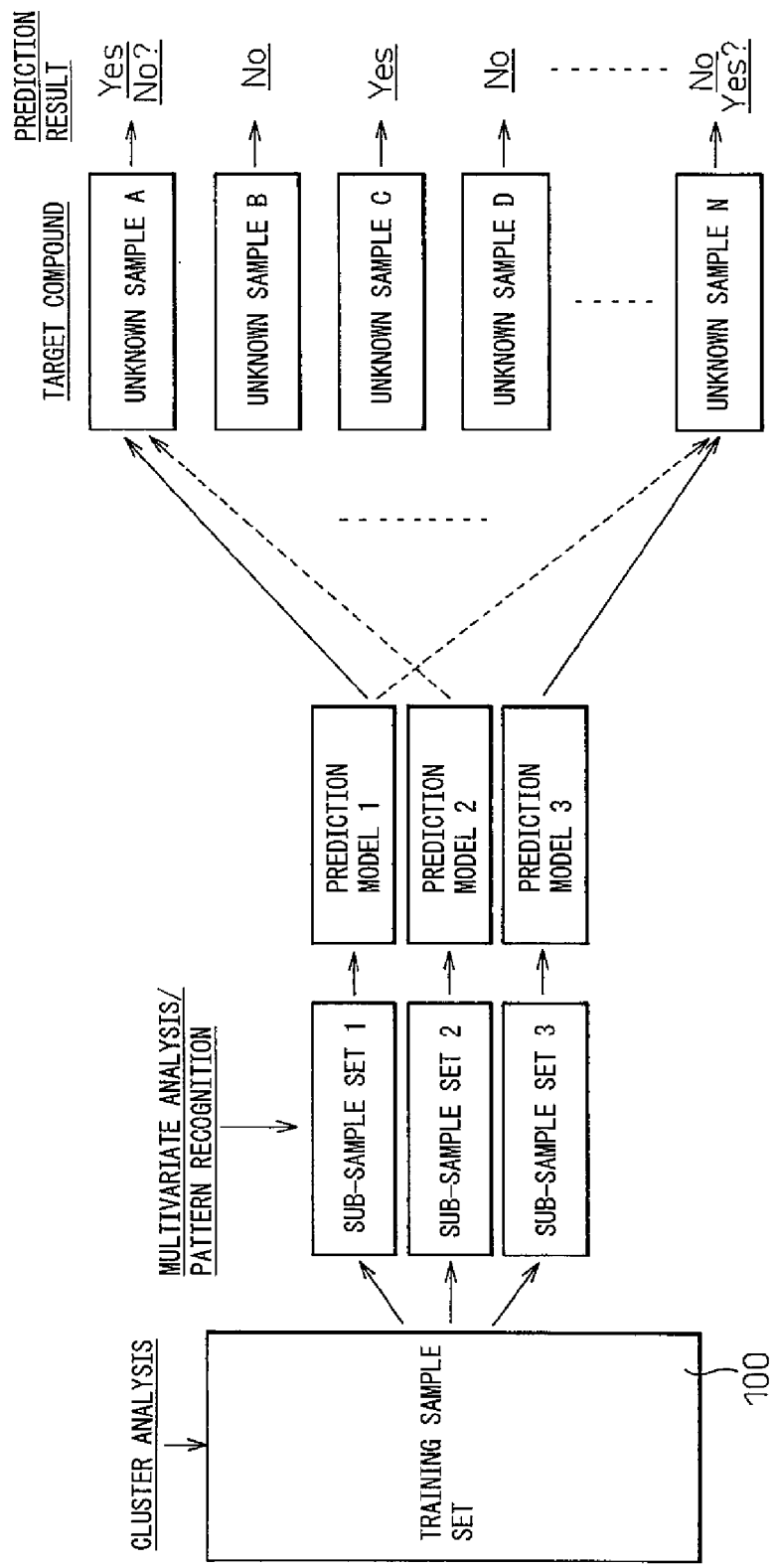

COMPOUND PROPERTY PREDICTION APPARATUS, PROPERTY PREDICTION METHOD, AND PROGRAM FOR IMPLEMENTING THE METHOD

CROSS-REFERENCE TO RELATED APPLICATION

This application is a continuation application based upon International Application No. PCT/JP2007/066286, filed on Aug. 22, 2007, the entire contents of which are incorporated herein by reference.

FIELD

The present invention relates to a compound property prediction apparatus and method for constructing a prediction model by statistically processing existing data and for predicting the properties of a compound whose properties are unknown by using the thus constructed prediction model; the invention also relates to a program for implementing such a method. In this patent specification, the properties of a compound include not only the electrical, magnetic, optical, and mechanical properties of the compound but also other properties it possesses, such as those related to safety (toxicity), pharmacological activity, and pharmacokinetics.

BACKGROUND

In modern society, predicting events in various fields or predicting the properties of substances based on data analysis is becoming increasingly important. In particular, with increasing awareness of worldwide environmental issues, as well as from the standpoint of animal welfare, expectations are growing for the practical implementation of techniques that predict various kinds of safety (toxicity) of chemical compounds by making full use of IT (Information Technology). However, it is known that the field of compound safety (toxicity) prediction is a field where it is very difficult to achieve high prediction rates. Furthermore, it is a difficult field that demands particularly high prediction rates, because failure of the prediction could have serious consequences (not only biologically but also ecologically (environmentally)).

A brief description will be given of the importance of the compound safety prediction and the special nature of the compound safety prediction field. The application field of safety prediction is extensive. Generally, in pharmaceutical related fields, safety prediction has been performed to predict the toxicity of pharmaceutical products and their side effects. The target of safety prediction in this field is a human being (biotoxicity), and if the prediction fails, many people would suffer serious or fatal side effects. In this respect, safety prediction in this field, unlike prediction tasks in other fields, demands significantly strict prediction accuracy.

In recent years, there has been increased interest in the importance of the safety prediction in environment related fields. This is because chemical compounds are substances (biotoxic substances) that greatly affect not only human beings but also the environment, i.e., the ecosystem, and all types of life that depend on the ecosystem. It is expected that governmental regulations on the environmental safety of chemical compounds will become more stringent than ever around the world.

For example, in the EU, a new regulation named REACH entered into force in June 2007. According to this regulation, every company using a chemical is obliged to evaluate the safety of that chemical and register the result of the evaluation; the scope of the regulation is extended to cover more than 30,000 kinds of existing chemicals (including chemicals whose production has empirically been approved without evaluating their safety). REACH is an unprecedentedly strict regulation as it is applied not only to the manufacturers of chemicals but also to the companies that use manufactured chemicals. Company activities in the EU would not be possible without meeting the requirements set by the regulation.

As described above, the trend is toward imposing strict restrictions on the evaluation tests of chemicals using animals, and sooner or later, animal testing for the development of new drugs will be banned. Already, in the EU, a ban on skin-related animal tests will commence in 2011. In the environmental toxicity evaluation as stipulated in the REACH regulation, since the number of chemicals to be evaluated is incomparably larger than that used in the development of a new drug, there arises not only the problem of animal testing but also the problem of time and cost needed to conduct experiments, and therefore, the use of IT as an ultra high-speed screening technique to substitute for experiments becomes an important issue in order to reduce the evaluation time and cost. Therefore there is a need to develop prediction techniques that can evaluate safety with the highest possible accuracy without conducting experiments. Since such techniques can simplify the work associated with REACH and other regulations, the authorities concerned recommend the development of such prediction techniques on a worldwide basis.

While compound safety prediction using IT has been attracting a great deal of attention as described above, it is not possible to achieve sufficiently high prediction accuracy with the present state-of-the-art prediction techniques because, unlike such fields as character recognition, not only are the structural formulas of compounds very complex, but also there are a great variety of compounds amounting to tens of millions of kinds and, on top of that, factors affecting toxicity are also complex. Furthermore, since low prediction rates would pose hazards due to the special nature of this field, it is important to achieve very high prediction reliability for the practical implementation of prediction techniques. Therefore, a general need always exists for the development of a method and apparatus for predicting the properties, in particular, the safety, of chemical compounds with very high accuracy.

FIG. 12 is a diagram illustrating an overview of a prior art prediction system which predicts the physical/chemical properties of compounds by using statistical techniques. In this system, first a training sample set 100 is prepared by collecting as many compounds as possible that have known values for the property about to be predicted (the prediction item). Then, a prediction model 102 is constructed by performing data analysis, such as multivariate analysis or pattern recognition, on the training sample set 100.

In the prediction execution stage, prediction results are obtained by applying the prediction model 102 constructed as described above to each of the compounds A to N (hereinafter called the unknown samples) whose properties are to be predicted. For example, in the case of a discriminant analysis for determining whether a compound has carcinogenicity, the prediction result YES means that it is determined that the compound has carcinogenicity, while NO means that it is determined that the compound does not have carcinogenicity.

Various attempts have been made to predict, for example, the toxicity of compounds by using techniques such as described above, but the reality is that prediction rates, as high as expected, have not yet been achieved. The prediction rate may normally be calculated based on the correctness of the predictions performed on unknown samples, but this would require that the actual effect be verified by animal testing, etc., which would be difficult to implement. Therefore in actual practice, one sample is taken as a tentative unknown sample from the training sample set, and the prediction is performed on the tentative unknown sample by using the prediction model generated from the remaining training sample set; then, the degree of accuracy of the prediction model, i.e., the prediction rate, is calculated based on the result of the prediction.

In a prediction system such as illustrated in FIG. 12, various strategies have been devised to improve the prediction rate. Such strategies include, for example, ingeniously designing a data analysis method for obtaining a prediction model, or classifying, based on various empirical criteria, a large number of compounds forming the training sample set, and constructing a prediction model for each classified class. In the former case, classification methods using such techniques as linear learning machine, discriminant analysis, Bayes linear discriminant analysis, Bayes nonlinear discriminant analysis, neural networks, SVM, KNN (K-Nearest Neighbor), etc., have been tried for use in the problem of classifying compounds into two classes, one having toxicity and the other having no toxicity, and recently it has been reported that high classification rates can be obtained with relative ease by the neural network or SVM methods (non-patent document 1).

However, while the classification rate improves with the neural network or SVM methods, the prediction rate drops. This is presumably because such analysis techniques tend to perform classification for the sake of classification while ignoring the chemical factors that lie behind the background of the classification. For this reason, the approach that aims to improve the prediction rate by ingeniously designing an analysis technique has, up to this date, not been successful in achieving good results.

In the prediction system illustrated in FIG. 12, one prediction model is generated from the training sample set. On the other hand, as described above, an attempt has been made to perform predictions by generating a plurality of prediction models from the training sample set and by applying one or more prediction models to each unknown sample.

FIG. 13 is a diagram providing an overview of such a prediction system. First, the large number of compounds forming the training sample set 100 are classified based on the basic structure or property of the compounds, to generate sub-sample sets 1, 2, and 3. Next, multivariate analysis or pattern recognition is performed on each sub-sample set, generating a prediction model 1 from the sub-sample set 1, a prediction model 2 from the sub-sample set 2, and a prediction model 3 from the sub-sample set 3.

In the prediction execution stage, the prediction is performed by applying the plurality of thus constructed prediction models to the unknown samples A to N. The problem here is which of the plurality of prediction models is to be applied, for example, to the unknown sample A. If the correct prediction model is not selected, there can occur cases where, when the prediction model 1 is applied to the unknown sample A, for example, the result YES is obtained but, when the prediction model 2 is applied, the result NO is obtained, and the reliability of the prediction thus degrades. Usually, all of the prediction models are applied to each unknown sample to obtain a plurality of prediction results, and after that, the final prediction result is determined by taking a majority among the plurality of prediction results.

However, even with this method, it is not possible to obtain sufficiently high prediction rates. As a possible solution, a prediction model generated from a sub-sample set containing samples having a structure similar to an unknown sample may be selected as the prediction model for that unknown sample, but since the structures of compounds are complex and diverse, there is not always a significant correlation between the sub-sample set and the unknown sample, and as a result, it is not possible to achieve a high prediction rate.

As described above, with the prediction system illustrated in FIG. 13, the classification rate of the training sample set increases because of the construction of a plurality of prediction models, but it falls short in improving the prediction rate.

Non-patent document 1: Kazutoshi Tanabe, Norihito Ohmori, Shuichiro Ono, Takahiro Suzuki, Takatoshi Matsumoto, Umpei Nagashima, and Hiroyuki Uesaka, "*Prediction of Carcinogenicity of Chlorine-containing Organic Compounds by Neural Network,*" *Comput. Chem. Jpn.*, Vol. 4., No. 3, pp. 89-100 (2005)

SUMMARY

The present invention has been devised to solve the above problem associated with the prior art compound property prediction method and apparatus, and an object of the invention is to provide a compound property prediction apparatus and method that can achieve high prediction rates by generating a prediction model accurately reflecting information concerning each particular compound whose properties are to be predicted; it is also an object of the invention to provide a program for implementing such a method.

MEANS FOR SOLVING THE PROBLEM

According to a first aspect of the invention, to solve the above problem, there is provided a compound property prediction apparatus including: a memory storing a training sample library in which a parameter value relating to a chemical structure and a value for a prediction item are preregistered for each individual one of a plurality of training samples; an input device which takes data concerning an unknown sample as input; a processor, coupled to said memory and said input device, programmed to calculate a parameter value for the unknown sample, based on the input data; and, based on the parameter value, calculate the degree of similarity between the unknown sample and individual training samples; construct a sub-sample set by extracting training samples whose degree of similarity to the unknown sample is not smaller than a threshold that starts at a predetermined value and is reduced as necessary to ensure that a predetermined minimum number of the training samples are included in the sub-sample set; construct a prediction model by performing data analysis on the sub-sample set; and calculate a prediction value for the prediction item by applying the constructed prediction model to the unknown sample.

According to a second aspect of the invention, to solve the above problem, there is provided a compound property prediction method including: acquiring values of a plurality of parameters for an unknown sample of a chemical compound; acquiring values of the plurality of parameters for each individual one of training samples; based on values of the plurality of parameters, calculating the degree of similarity between the unknown sample and individual training samples; constructing a sub-sample set by extracting training samples whose degree of similarity to the unknown sample is not smaller than a threshold that starts at a predetermined value and is reduced as necessary to ensure that a predetermined minimum number of the training samples are included in the sub-sample set; constructing a prediction model by performing data analysis on the sub-sample set; and calculating a prediction item representing at least one physical property of the chemical compound by applying the constructed prediction model to the unknown sample.

According to a third aspect of the invention, to solve the above problem, there is provided a compound property prediction program for causing a computer to perform a process including: acquiring values of a plurality of parameters for an unknown sample; acquiring values of the plurality of parameters for each individual one of training samples; based on the values of the plurality of parameters, calculating the degree of similarity between the unknown sample and the individual one training sample; constructing a sub-sample set by extracting training samples whose degree of similarity to the unknown sample is not smaller than a predetermined threshold value; constructing a prediction model by performing data analysis on the sub-sample set; and calculating a prediction item by applying the constructed prediction model to the unknown sample.

If there are a plurality of unknown samples similar in structure, the prediction model may be constructed for one particular unknown sample in accordance with the method, apparatus, and program of the present invention; in this case, the degree of similarity between that one particular unknown sample and each of the other unknown samples is calculated and, for each of such other samples having high similarity, the prediction result is acquired by applying to it the prediction model constructed for the one particular unknown sample.

EFFECT OF THE INVENTION

According to the compound property prediction apparatus, method, and program of the present invention, the degree of similarity between an unknown sample and each individual one of training samples is calculated; then, a sub-sample set is constructed by extracting training samples whose degree of similarity to the unknown sample is not smaller than a predetermined value, and a prediction model is constructed by performing data analysis on the sub-sample set. The prediction model thus constructed based on the sub-sample set containing samples having high similarity to the unknown sample strongly reflects the unique features of the unknown sample and contains little noise information that can cause an erroneous prediction result in the prediction of the unknown sample (such noise information primarily occurs when a compound entirely different in structure from the unknown sample is contained in the training sample set). Accordingly, high prediction accuracy can be achieved by applying this prediction model to the unknown sample.

BRIEF DESCRIPTION OF THE DRAWINGS

FIG. 1 is a block diagram explaining the basic concept of the present invention.

FIG. 2A is a flowchart illustrating the sequence of operations performed in accordance with a compound property prediction method according to the present invention.

FIG. 2B is a flowchart illustrating the sequence of operations performed in accordance with another compound property prediction method according to the present invention.

FIG. 4 is a diagram illustrating a portion of the contents of a training sample library.

FIG. 5 is a diagram illustrating another portion of the contents of the training sample library.

FIG. 11 is a diagram illustrating a comparison of prediction results between the method of the present invention and a prior art method.

FIG. 12 is a diagram illustrating an overview of a prediction system according to the prior art.

FIG. 13 is a diagram providing an overview of another prediction system according to the prior art.

DESCRIPTION OF EMBODIMENTS

Figure 3:
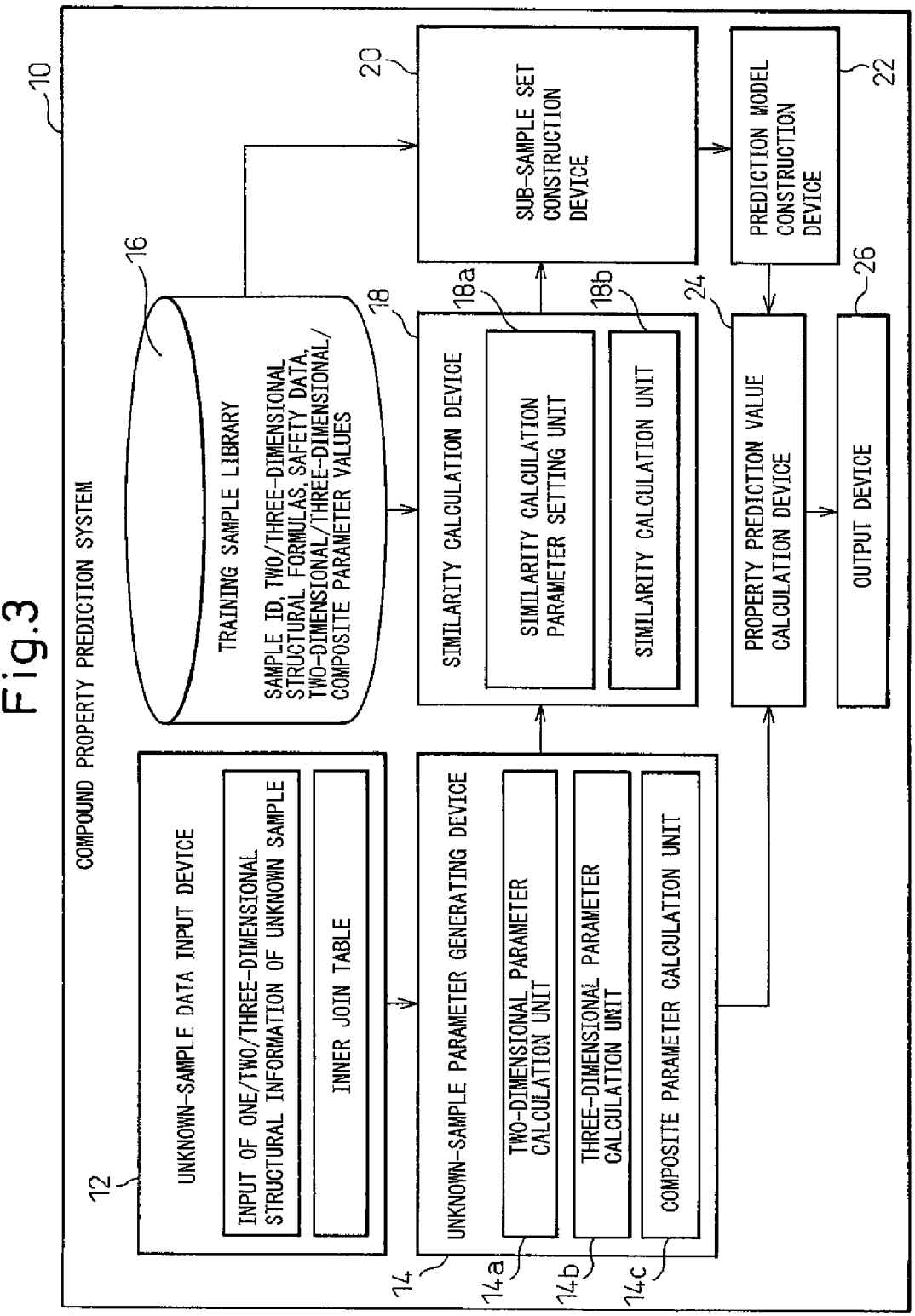
FIG. 3 is a block diagram illustrating the configuration of a compound property prediction system according to one embodiment of the present invention.

Compound safety (toxicity) prediction demands a particularly high prediction rate, because failure of prediction could have serious consequences. Therefore, the most important consideration in the construction of a compound property prediction model, in particular, a safety prediction model, is to construct a prediction model having high accuracy for each particular unknown sample, not to construct a prediction model having high accuracy for an unspecified number of unknown samples. If a prediction model is constructed aiming to cover an unspecified number of unknown samples, the resulting prediction model will contain information that may be important for one particular unknown sample but is mostly noise for other unknown samples, and hence a limitation on the improvement of the prediction rate.

In view of this, the present invention proposes so-called tailor-made modeling in which a prediction model is constructed that efficiently reflects information needed for predicting the properties of each particular unknown sample and the prediction is performed by applying the thus constructed prediction model only to that particular unknown sample. The most important feature of the tailor-made modeling is that one prediction model corresponds to one particular unknown sample. The prediction model thus constructed contains information mostly important for that particular unknown sample but very little noise information. As a matter of course, the prediction rate greatly improves.

FIG. 1 is a conceptual diagram illustrating the basic concept of a compound property prediction method and apparatus according to the present invention. First, structure data is prepared for an unknown sample A which is a compound whose properties are to be predicted. The unknown sample A may be an arbitrarily selected sample. Next, the samples contained in a training sample set 1 are screened for structural similarity to the unknown sample A, and a sub-sample set A is constructed using samples detected as being similar to the unknown sample A (that is, samples that contain information related to the unknown sample A). Then, a prediction model A is constructed by performing data analysis (multivariate analysis or pattern recognition) on the thus generated sub-sample set A.

In the present invention, since the prediction model A for the unknown sample A is generated from a set of training samples (sub-sample set A) similar in structure to the unknown sample A, the prediction model A contains information reflecting the detail features of the unknown sample A but does not contain any noise information. As a result, the properties of the unknown sample A can be predicted with high accuracy, provided that the prediction model A is applied to the unknown sample A.

The above sequence of operations is repeated for each of the subsequent unknown samples B, C, . . . , N; in this way, the prediction models A to N that accurately reflect the structural features of the respective unknown samples A to N are obtained. By applying these prediction models to the respective unknown samples, the properties of the unknown samples can be predicted with high accuracy.

FIG. 2A is a flowchart illustrating the sequence of operations when predicting the properties of an unknown sample in accordance with the basic concept of the present invention. First, in step S1, data of the unknown sample is entered into the property prediction system. The data of the unknown sample refers to data representing the one-dimensional, two-dimensional, and three-dimensional structures of the compound. In the next step S2, parameter values relating to the structures of the compound are calculated based on the entered data. When each prediction item is expressed as a dependent variable, each parameter corresponds to an explanatory variable. According, step S2 is a step that calculate the values of the explanatory variables predefined for the unknown sample.

In step S3, the values of the same parameters as those generated for the unknown sample are obtained for each of the samples contained in the training sample set. The training sample set is constructed from samples for which the value for the designated prediction item, i.e., the value of the dependent variable, is known. Therefore, if the values of the parameters needed for the prediction are generated in advance for each sample and stored in a library, the parameter values of each training sample can be easily obtained by referring to the library when constructing a prediction model for any unknown sample.

Next, the degree of structural similarity between the unknown sample and each individual training sample is calculated (step S4) based on the parameter values obtained in steps S2 and S3. In step S5, the degree of similarity calculated in step S3 is compared with a predetermined reference value, and a sub-sample set is constructed by extracting training samples whose degree of similarity is not smaller than the reference value. In step S6, a prediction model is constructed by performing data analysis using the thus generated sub-sample set. In step S7, the value for the prediction item, i.e., the value of the dependent variable, is calculated by applying the prediction model constructed in step S6 to the parameter values of the unknown sample. A highly accurate prediction result can thus be obtained.

If there are a plurality of unknown samples for which the value of the dependent variable is to be calculated, the degree of structural similarity between the plurality of unknown samples may be calculated, and within each group of unknown samples having high similarity, a prediction model may be constructed for one particular unknown sample in accordance with the sequence of operations illustrated in FIG. 2; in this case, the prediction model thus constructed is also applied to the other unknown samples similar in structure.

FIG. 2B is a diagram illustrating the sequence of operations when there are a plurality of unknown samples. In step S11, data of the unknown samples A to N are entered. In step S12, the parameter values of the unknown samples A to N are generated based on the entered data. In step S13, the degree of similarity between the unknown samples A to N is calculated based on the parameter values generated in step S12. In step S14, based on the degree of similarity calculated in step S13, unknown samples similar to the sample A are extracted to construct a group of samples similar to the unknown sample A.

When the preprocessing for the plurality of unknown samples A to N is completed as described above, the process proceeds to step S15 and subsequent steps to generate the sub-sample set A and construct the prediction model A for the unknown sample A. More specifically, the parameter values of each training sample are obtained in step S15, the degree of similarity between the unknown sample A and each training sample is calculated in step S16, and the sub-sample set A is generated in step S17. In step S18, the prediction model A is constructed by performing data analysis on the sub-sample set A generated in step S17.

When the prediction model A strongly reflecting the features of the unknown sample A is constructed as described above, the value for the prediction item is calculated by applying the prediction model A to the unknown sample A. The same prediction model A is also applied to each of the unknown samples classified as samples similar to the unknown sample A in step S14; in this way, the value for the prediction item is calculated for the respective unknown samples.

Since each unknown sample in the similar sample group is similar in structure to the unknown sample A, high prediction accuracy can be expected even when the prediction model A constructed specifically for the unknown sample A is applied to the unknown samples contained in the group. However, this technique, i.e., the method illustrated in FIG. 2B, is not suitable for applications where high prediction accuracy is an important requirement, since the prediction accuracy is not as high as that obtained for the unknown sample A. On the other hand, when handling, for example, a large number of unknown samples or similar compounds (for example, a group of homologous compounds), the processing speed and cost needed for the prediction becomes a problem; in such cases, the above method provides a suitable approach.

In the flowchart illustrated in FIG. 2B, steps S11 to S13 may be carried out by separating them from this flowchart, and the prediction value may be calculated by applying, for example, the prediction model constructed in step S6 in the flowchart of FIG. 2A to each individual sample in the similar unknown sample group constructed in step S14.

FIG. 3 is a block diagram illustrating the configuration of a compound property prediction system according to one embodiment of the present invention. As illustrated, the compound property prediction system 10 includes an unknown-sample data input device 12, an unknown-sample parameter generating device 14, a training sample library 16, a similarity calculation device 18, a sub-sample set construction device 20, a prediction model construction device 22, a property prediction value calculation device 24, and a prediction result output device 26.

The unknown-sample data input device 12 takes, as input to the system 10, information describing the one-dimensional, two-dimensional, or three-dimensional structure of the compound whose properties are to be predicted, and obtains an inner join table by converting the information into numeric data that can be used by the system 10. The inner join table is a table that stores the structural formulas of chemical compounds in the form of a two-dimensional matrix of numeric data. Input data items include 1) chemical structural formula (two- or three-dimensional), 2) sample name and sample ID, and 3) other related information. The structural formula can be entered in an interactive manner using a graphics system, or entered directly from an existing file. To enter chemical structural information and convert it into numeric data, various systems have been developed and made available for use.

The unknown-sample parameter generating device 14 calculates the values of various explanatory variables, i.e., the values of various parameters, based on the structure data entered for each unknown sample. The parameter generating device 14 usually includes a two-dimensional parameter calculation unit 14a, a three-dimensional parameter calculation unit 14b, and a composite parameter calculation unit 14c. The two-dimensional parameter calculation unit 14a calculates two-dimensional parameters based on the two-dimensional data of the compound in the inner join table, and the three-dimensional parameter calculation unit 14b calculates three-dimensional parameters based on the three-dimensional data of the compound in the inner join table.

When calculating a three-dimensional parameter from two-dimensional data, first the two-dimensional data is converted into three-dimensional data by a three-dimensional coordinate calculation unit (not illustrated), and then the three-dimensional parameter is calculated. The composite parameter calculation unit 14c calculates composite parameters based on the calculated two-dimensional and three-dimensional parameters.

The two-dimensional parameters include 1) molecular parameters, for example, molecular weight, atomic species, number of atoms, bond species, number of bonds, etc., 2) topological parameters, for example, molecular bond index, Hosoya index, Balaban parameter, etc., 3) property parameters, for example, molecular refractive index, parachor, Log P, etc., and 4) other parameters, for example, partial structure parameters (information on occurrence (1, 0) and frequency of occurrence), partial charge parameters, etc.

The three-dimensional parameters include 1) three-dimensional shape parameters, for example, molecular surface area, molecular volume, molecular shadow parameters, molecular moment parameters, etc., and 2) electron/energy related parameters, for example, molecular orbital method parameters (electron density, polarizability, HOMO/LUMO, etc.), molecular dynamic parameters (molecular energy, bonding energy, repulsive energy, etc.), molecular kinetic parameters, etc. The composite parameters include parameters created by joining molecular shape and electron information parameters, for example, CPSA (molecular surface area+molecular surface electron density information) parameters and other operator parameters (the type of operation to be performed between parameters (+, 1, ×, /, etc.).

In the training sample library 16, there are registered, for each sample in the training sample set, the sample ID, the two- or three-dimensional structural formula of the sample, known data concerning safety (toxicity), and two-dimensional, three-dimensional, or composite parameter values.

FIGS. 4 and 5 illustrate examples of the registered contents of the training sample library 16. FIG. 4 illustrates, for each training sample, the sample ID number, the two-dimensional structural formula of the sample, and the CAS number. FIG. 5 illustrates, for each training sample, known safety data (fish toxicity LC50) 51 and the values of various parameters (explanatory parameters) 52. While FIG. 5 primarily illustrates the parameters related to the structure of each sample compound, it will be recognized that various other parameters described above are also registered in the library. The safety data (dependent variable) 51 illustrates fish toxicity (code information 0 (not toxic) or 1 (toxic), as judged by 50% lethal concentration (LC50)), but various kinds of other available safety data such as Ames test results are also registered in this dependent variable.

The similarity calculation device 18 includes a unit 18a for setting similarity calculation parameters automatically or by user selection, and a similarity calculation unit 18b. The similarity calculation unit 18b can set or change the threshold value used to determine whether a training sample is similar to an unknown sample. Examples of similarly calculation techniques include 1) an approach using a Tanimoto coefficient, 2) a technique that makes a selection within a parameter value range, 3) a technique that uses multivariate analysis or pattern recognition, for example, a method that calculates distance between samples in N-dimensional space, a method that uses various clustering analysis techniques, etc., and 4) a technique based on various empirical classification criteria, for example, a technique based on the classification of compounds (aromatic/non-aromatic, acyclic/monocyclic/polycyclic, etc.), etc. Any of these techniques may be used. The details of these techniques will be described in detail later.

The sub-sample set construction device 20 extracts from the training sample set the training samples whose degree of similarity calculated by the similarity calculation device 18 is not smaller than the predetermined value (threshold value), and groups them together to form a sample set for constructing a prediction model. The sample set thus formed is hereinafter called the sub-sample set. If the number of samples forming the sub-sample set falls short of a predetermined number, the similarity threshold value used in the similarity calculation device 18 may be changed so that the sub-sample set construction device 20 can extract the predetermined or larger number of samples to form the sub-sample set. This is done in order to ensure the reliability of data analysis.

The prediction model construction device 22 constructs a prediction model by performing data analysis on the sub-sample set produced by the sub-sample set construction device 20. For the analysis data (parameter values, etc.), the system of the present embodiment uses the data registered in the training sample library 16. The prediction model is constructed in various forms depending on the data analysis techniques used. For example, the prediction model takes the form of a discriminant function in the case of a two-class classification method, a regression equation in the case of a fitting method, a network in the case of a neural network, a set of discriminant functions in the case of AdaBoost, a multi-stage combinational discriminant function in the case of a KY method (two-class classification), a combination of a multi-stage regression equation and a discriminant function in the case of a KY method (fitting), a hierarchical discriminant function in the case of SVM, a plurality of discriminant functions in the case of an ALS method, a regression equation in the case of a PLS method, and a distance matrix of samples in the case of a KNN method. These data analysis techniques can be suitably selected according to the kind of the sample and the purpose of the prediction.

For the construction of the prediction model, the selection of the final parameter set to be used for the construction of the prediction model (feature extraction) and the isolation and removal of samples unwanted for data analysis may be performed as preparatory steps. The prediction model construction device 22 first removes noise parameters by performing various kinds of feature extraction. The kinds of feature extraction to be performed and the order in which they are performed differ depending on the data analysis techniques used which include, for example, two-class classification, multi-class classification, and fitting and other methods. A typical example of two-class classification using a linear classifier will be briefly described below.

In the example here, noise parameters are removed by applying the following feature extraction techniques in the order listed.

(1) Removal of parameters containing missing data.
(2) Frequency of occurrence of same values.
(3) Correlation (simple correlation) coefficient
(4) Multiple correlation coefficient
(5) Fischer ratio
(6) Weight-sign method
(7) Variance-weighted method
(8) Feature extraction by genetic algorithm Today, many other feature extraction techniques are known, and there are also known many feature extraction techniques that strongly depend on the data analysis techniques used; therefore, other techniques may be used in addition to the above listed techniques.

In addition to removing noise parameters by the above feature extraction, it is also necessary to remove noise samples. Further, from the standpoint of the reliability of the data analysis itself, the minimum number of samples needed to construct a highly reliable prediction model has a strong correlation with the number of parameters used for the construction of the prediction model. In the construction of the prediction model, if the number of samples in the sub-sample set turns out to be small compared with the number of parameters, information to that effect is fed back to the sub-sample set construction device 20 which then changes the similarity threshold value used in the similarity calculation device 18 and extracts from the library 16 the needed number of samples for the data analysis; by so doing, the prediction model can be constructed while maintaining the reliability of the data analysis.

The prediction model construction device 22 may be configured to construct one prediction model by applying one particular data analysis technique to the sub-sample set, or may alternatively be configured to construct a plurality of prediction models by applying a plurality of data analysis techniques.

The property prediction value calculation device 24 calculates the prediction value, i.e., the value for the prediction item, by applying the one or plurality of prediction models constructed by the prediction model construction device 22 to the parameter values generated by the unknown-sample parameter generating device 14. The prediction value includes the determination of the class to which the unknown sample belongs. When a plurality of prediction models are generated, a plurality of prediction values are calculated by applying the plurality of prediction models to the unknown sample, and in the case of class classification, for example, the prediction result is determined by majority rule. In the case of fitting, an average value taken, for example, over a plurality of prediction results, is used. Alternatively, a minimum/maximum value may be used, or all the prediction results may be displayed so that the final decision can be made by human experts, or a decision algorithm may be generated in advance in the form of a program.

The output device 26 outputs the prediction result calculated by the property prediction value calculation device 24 and its related information in the form of a graph or text information. The related information includes the prediction item, compound information, sub-sample set information, information concerning the parameter set, data analysis technique related information, and prediction model information.

Next, a description will be give of the various compound structural similarity calculation techniques that can be used in the similarity calculation device 18.

[Approach Using Tanimoto Coefficient]

For an unknown sample X and a training sample Y between which the degree of similarity is to be calculated, the presence or absence of various partial structures, functional groups, etc., is examined by referring to the unknown-sample parameter generating device 14 and the training sample library 16, and the samples are each represented by a bit string of 0s and 1s as illustrated in Table 1 below.

TABLE 1

| | BENZENE RING | PIPERIDINE RING | COOH | $NH_2$ | Cl | Br |
|---|---|---|---|---|---|---|
| SAMPLE X | 1 | 1 | 1 | 1 | 0 | 0 |
| SAMPLE Y | 1 | 1 | 1 | 0 | 1 | 1 |

When A, B, and C are defined as illustrated below, the Tanimoto coefficient is defined as $$T = C/(A+B-C) \qquad \text{(Equation 1)}$$

A: Number of bits that are set to 1 in sample X
B: Number of bits that are set to 1 in sample Y
C: Number of bits that are set to 1 in both sample X and sample Y From the above equation (1), if the two samples X and Y are identical in structure, the Tanimoto coefficient T is equal to 1, and as the difference in structure becomes larger, the value of the coefficient T approaches 0. Accordingly, if the reference value α of the Tanimoto coefficient, which is used to determine whether the training sample is similar to the unknown sample, is determined in advance, then similar samples can be extracted by comparing the result of each similarity calculation with the reference value α.

[Technique that Makes Selection within Parameter Value Range]

A compound is defined by various parameters. These parameters are, from the simplest one, molecular weight, molecular volume, molecular surface area, molecular projected area, number of atoms/bonds (in the entire compound and in each atomic/bond species), and various properties (for example, Log P (distribution coefficient), MR (molecular refractive index), parachor, melting point, boiling point, etc.). There are two techniques, i.e., one that specifies one particular parameter and uses its value as a filter, and the other that specifies two or more parameters and uses their values as filters.

When using the value of one particular parameter A as a filter, the value "a" of the parameter A is calculated for the unknown sample X, and predetermined widths "b" and "c" are added before and after that value. After thus determining the filter width ranging from (a−b) to (a+c), training samples whose parameter A has a value "x" larger than (a−b) but smaller than (a+c) are extracted to form the sub-sample set for the construction of a prediction model.

When using the values of a plurality of parameters A and B as filters, the same processing as when using the value of one particular parameter described above is performed for each of the parameters A and B, and the sub-sample sets produced based on the respective parameters A and B are ANDed or ORed to produce the final sub-sample set.

As an example, when the molecular weight is used as a filtering parameter, training samples whose molecular weight is larger than (S−100) but smaller than (S+200), where S is the molecular weight of the unknown sample X, are extracted to form the sub-sample set for the construction of a prediction model.

On the other hand when the molecular weight and the Log P value are used as filtering parameters, training samples whose molecular weight is larger than (S−100) but smaller than (S+200), where S is the molecular weight of the unknown sample X, are extracted to form the sub-sample set A, and then training samples whose Log P value is larger than (P'−5.0) but smaller than (P'+5.0), where P' is the Log P value of the unknown sample X, are extracted to form the sub-sample set B. Next, the thus formed sub-sample sets A and B are ANDed or ORed to produce the sub-sample set for the construction of a prediction model.

[Technique Using Multivariate Analysis or Pattern Recognition]

This technique is implemented by one of two methods, 1) a method that calculates distance between samples in N-dimensional space and 2) a method that uses various clustering techniques. In the method 1), multivariate analysis or pattern recognition, using parameter values, is performed on a training sample set containing an unknown sample, to construct an N-dimensional space defined by N parameters. In this case, the distance between each sample in the N-dimensional space can be calculated; therefore, training samples whose distance to the unknown sample falls within a predetermined range are extracted as similar samples to produce the sub-sample set for the construction of a prediction model.

Figure 6:
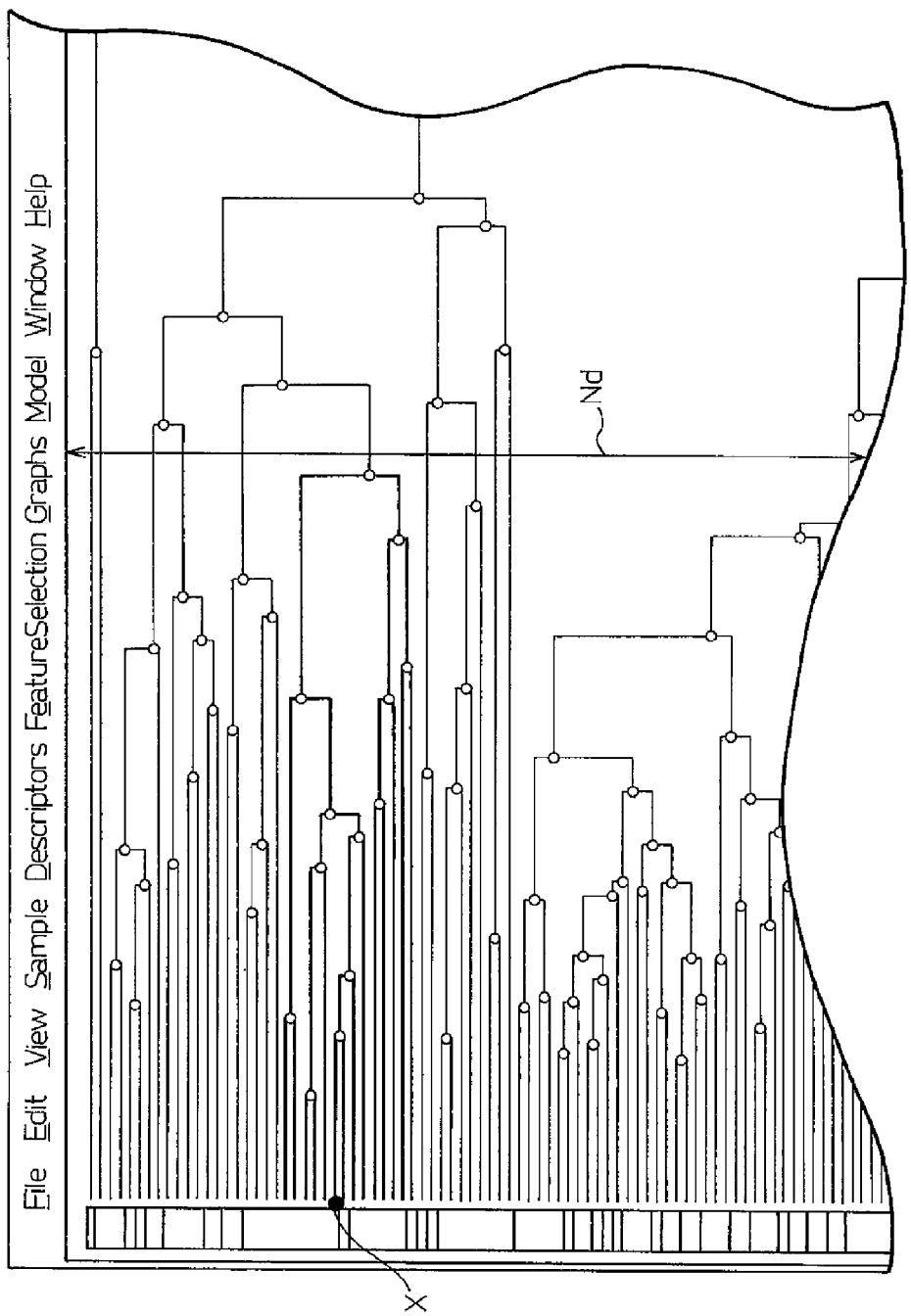
FIG. 6 is a diagram illustrating a dendrogram used in cluster analysis.

In the method 2), clustering analysis, using parameter values, is performed on a training sample set containing an unknown sample, and training samples belonging to the same cluster as the unknown sample or to a cluster close to it are extracted to produce the sub-sample set for the construction of a prediction model. In particular, in hierarchical clustering that uses a dendrogram such as illustrated in FIG. 6, training samples belonging to the layers lower than a given node Nd and centered around the cluster to which the unknown sample X belongs are extracted to produce the sub-sample set. In FIG. 6, the training samples lying within the range enclosed by thick lines are selected to produce the sub-sample set. In a non-hierarchical clustering technique, a list in which a set of sample compounds is classified into clusters (groups) is output; therefore, using this list, the cluster that contains the unknown sample may be taken as a similar sample group, and this sample group may be used directly as the sub-sample set.

The configuration and operation of the system illustrated in FIG. 3 will be described in further detail with reference to the flowcharts of FIGS. 7 to 11.

Figure 7:
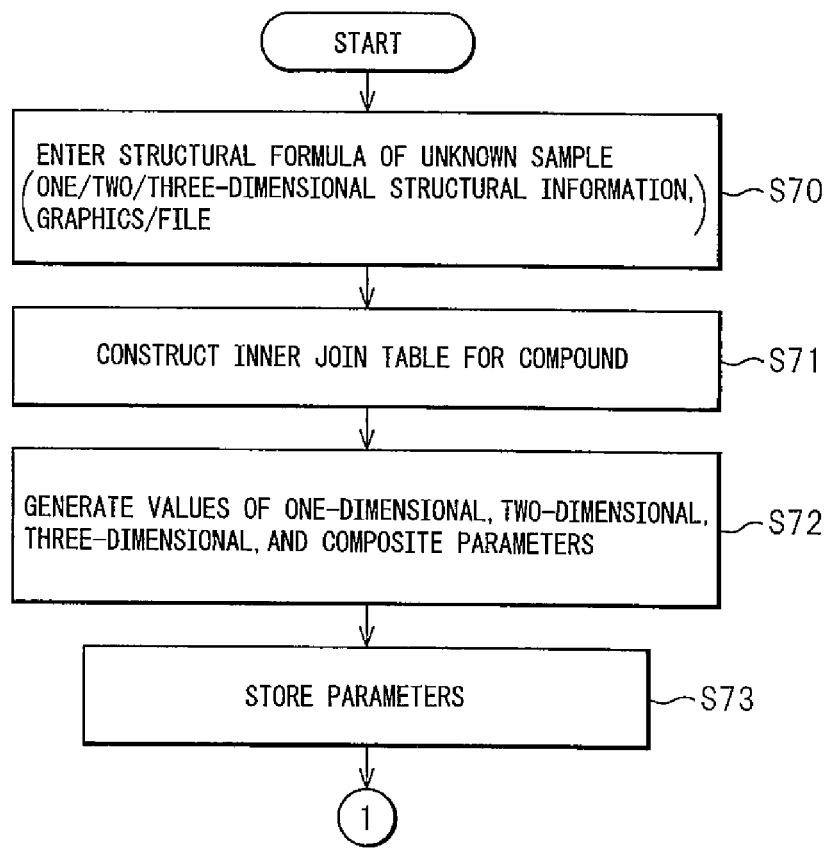
FIG. 7 is a flowchart illustrating the sequence of operations performed within an unknown-sample data input device and an unknown-sample parameter generating device in the system of FIG. 3.

FIG. 7 is a flowchart illustrating the sequence of operations performed within the unknown-sample data input device 12 and the unknown-sample parameter generating device 14 in the compound property prediction system illustrated in FIG. 3. When the two-dimensional structural formula of the unknown sample X is entered into the input device 12 by the user, for example, via a graphics display (step S70), the entered two-dimensional structural formula is converted into numeric data to construct an inner join table for the compound (step S71). Based on the inner join table, the unknown-sample parameter generating device 14 generates various parameters (step S72). The generated parameters are stored, for example, in an internal memory (not illustrated) of the system, along with the sample ID and the two- or three-dimensional structural formula of the sample (step S73).

Figure 8:
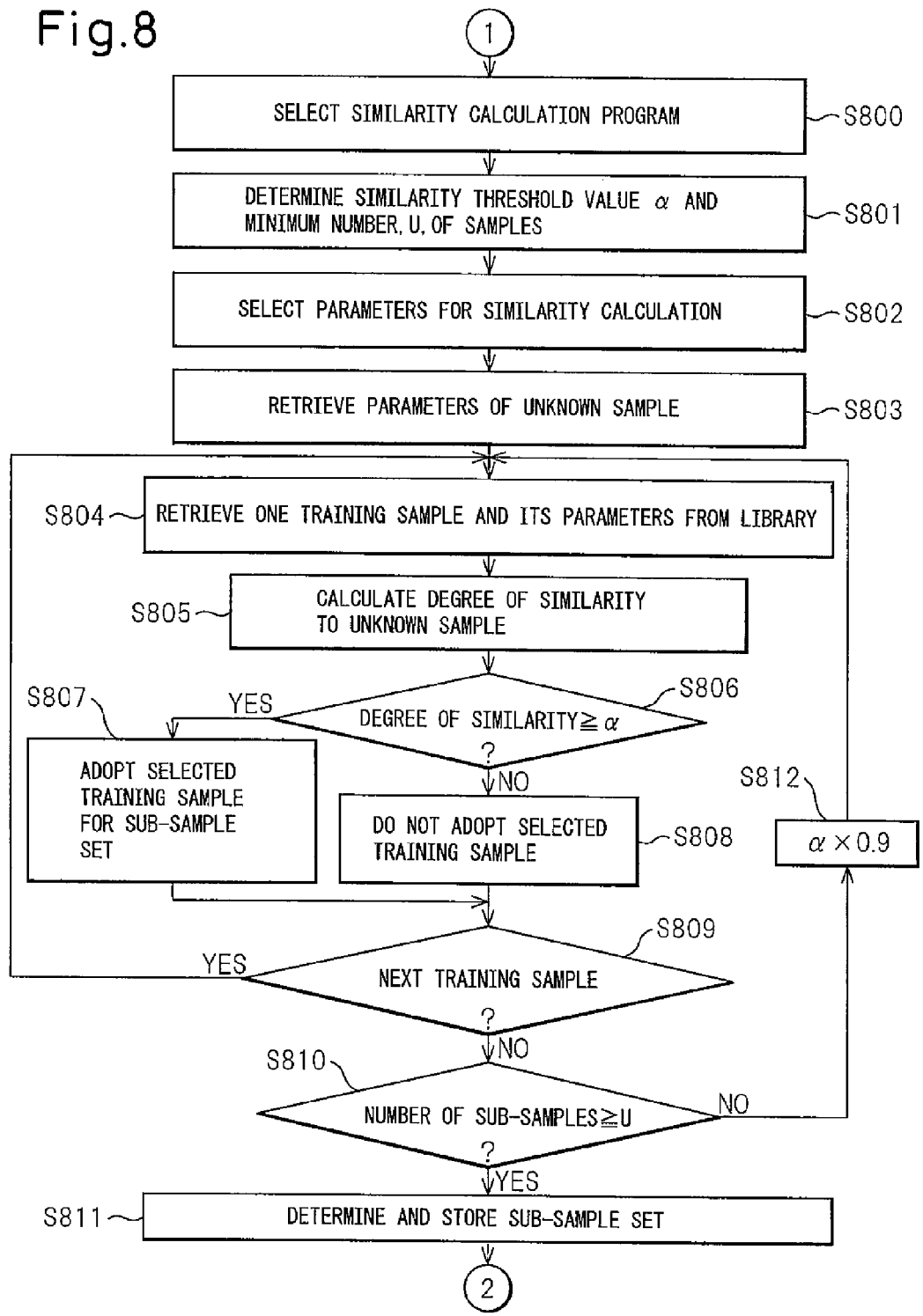
FIG. 8 is a flowchart illustrating the sequence of operations performed within a similarity calculation device in the system of FIG. 3.

FIG. 8 is a flowchart illustrating the sequence of operations performed within the similarity calculation device 18 and the sub-sample set construction device 20. If a plurality of similarity calculation programs, each using a different algorithm, are stored in the similarity calculation device 18, an appropriate program is selected in step S800. The selection may be made by the user, or provisions may be made to automatically select the corresponding program according to the prediction item, etc.

In step S801, the value of the similarity decision threshold $\alpha$, i.e., the reference value used to judge the similarity between the unknown sample X and each training sample, is determined. The threshold value $\alpha$ may also be appropriately determined by the user, or a value predetermined by the system may be used. In step S801, the minimum number of samples, U, needed to construct the sub-sample set is also determined. The minimum needed number of sub-samples is determined here because the reliability of the data analysis decreases if the number of sub-samples extracted by similarity calculation falls far short of the needed number.

In step S802, a parameter set for similarity calculation is selected. The selection of the parameter set may be automatically made by the program selected in step S800, or the user may select a suitable parameter set.

In step S803, the parameter values of the unknown sample are retrieved, for example, from the internal memory, and in step S804, the ID number of one particular training sample Y1 and its parameter values are retrieved from the training sample library 16; then, based on the thus retrieved parameter values, the degree of similarity between the unknown sample X and the training sample Y1 is calculated (step S805).

In step S806, it is determined whether or not the degree of similarity calculated in step S805 is equal to or larger than the threshold value $\alpha$ determined in step S802. If it is equal to or larger than $\alpha$ (YES in step S806), the training sample Y1 is adopted as a sample for the sub-sample set (step S807), but if it is smaller than $\alpha$ (NO in step S806), the training sample Y1 is not adopted as a sub-sample (step S808). In step S809, the training sample library 16 is checked to see if there is any training sample whose degree of similarity is not yet calculated; if there is any such sample (YES in step S809), the process returns to step S804 to repeat the above cycle of operations.

If NO in step S809, that is, if the similarity calculation is completed for all the samples in the training sample library 16, the process proceeds to step S810 to determine whether or not the number of selected samples is equal to or larger than the threshold U. If it is equal to or larger than the threshold U (YES in step S810), all the training samples adopted as sub-samples in step S807 are presented in the form of a list, and these samples are determined and stored as the sub-sample set (step S811).

If it is determined in step S810 that the number of samples is smaller than U (NO in step S810), the threshold value $\alpha$ is multiplied, for example, by 0.9 (step S812), and the process returns to step S804 to repeat the above cycle of operations.

When the final sub-sample set is presented in the form of a list in step S811, its information is sent to the sub-sample set construction device 20. Upon receiving the sub-sample set information, the sub-sample set construction device 20 accesses the training sample library 16 and retrieves parameter information for each individual sub-sample. The parameter information here includes other parameters than those used for similarity calculation, and data relating to the prediction item, for example, the value of fish toxicity (LC50).

Figure 9:
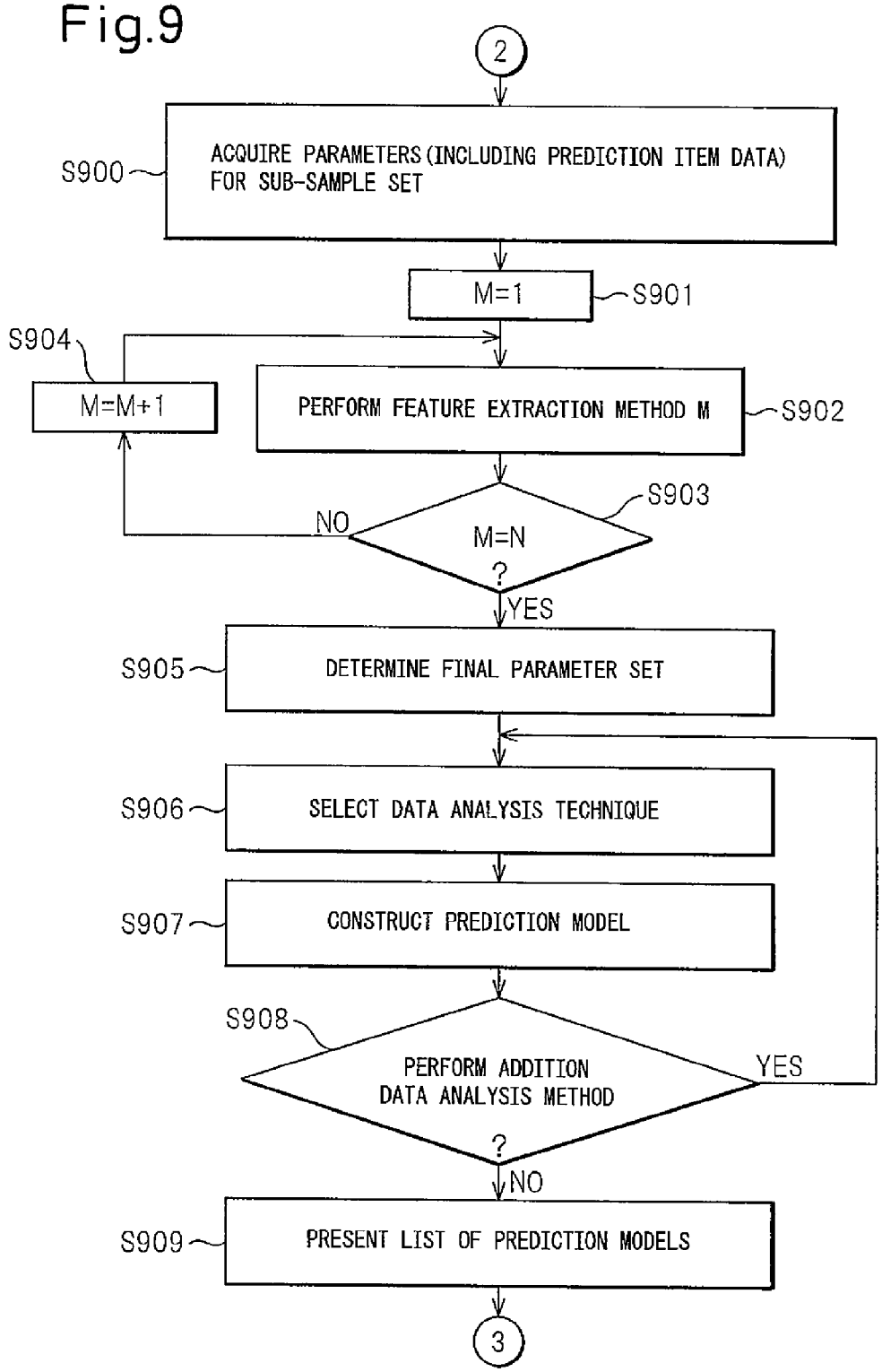
FIG. 9 is a flowchart illustrating the sequence of operations performed within a prediction model construction device in the system of FIG. 3.

FIG. 9 is a flowchart illustrating the sequence of operations performed within the prediction model construction device 22 illustrated in FIG. 3. In step S900, the parameter values of the sub-samples are acquired by referring to the sub-sample set construction device 20. Next, a plurality of feature extraction methods are performed in order to remove noise parameters unwanted for data analysis. First, in step S901, M is set to 1, and in step S902, the first feature extraction method is performed. The previously listed feature extraction methods (1) to (8), for example, are performed in the order listed. In step S903, it is determined whether M=N, i.e., whether the feature extraction method currently performed is the final (Nth) feature extraction method; if NO, M is incremented by 1 in step S904, and the process returns to step S902 to repeat the above cycle of operations.

Feature extraction is performed in order to remove unwanted parameters (noise parameters); therefore, if the answer is YES in step S903, i.e., if it is determined that all the feature extraction methods preregistered in the prediction model construction device 22 have been performed, the process proceeds to step S905 where the final parameter set is determined. In step S906, one particular data analysis technique is selected for the final parameter set, and in step S907, a prediction model is constructed by performing the thus selected data analysis technique.

In step S908, it is determined whether an addition data analysis method is to be performed or not; if an addition data analysis method is to be performed (YES in step S908), the process returns to step S906 to repeat the above cycle of operations. When all of the desired data analysis methods have been performed (NO in step S908), all of the constructed prediction models are presented in the form of a list.

Figure 10:
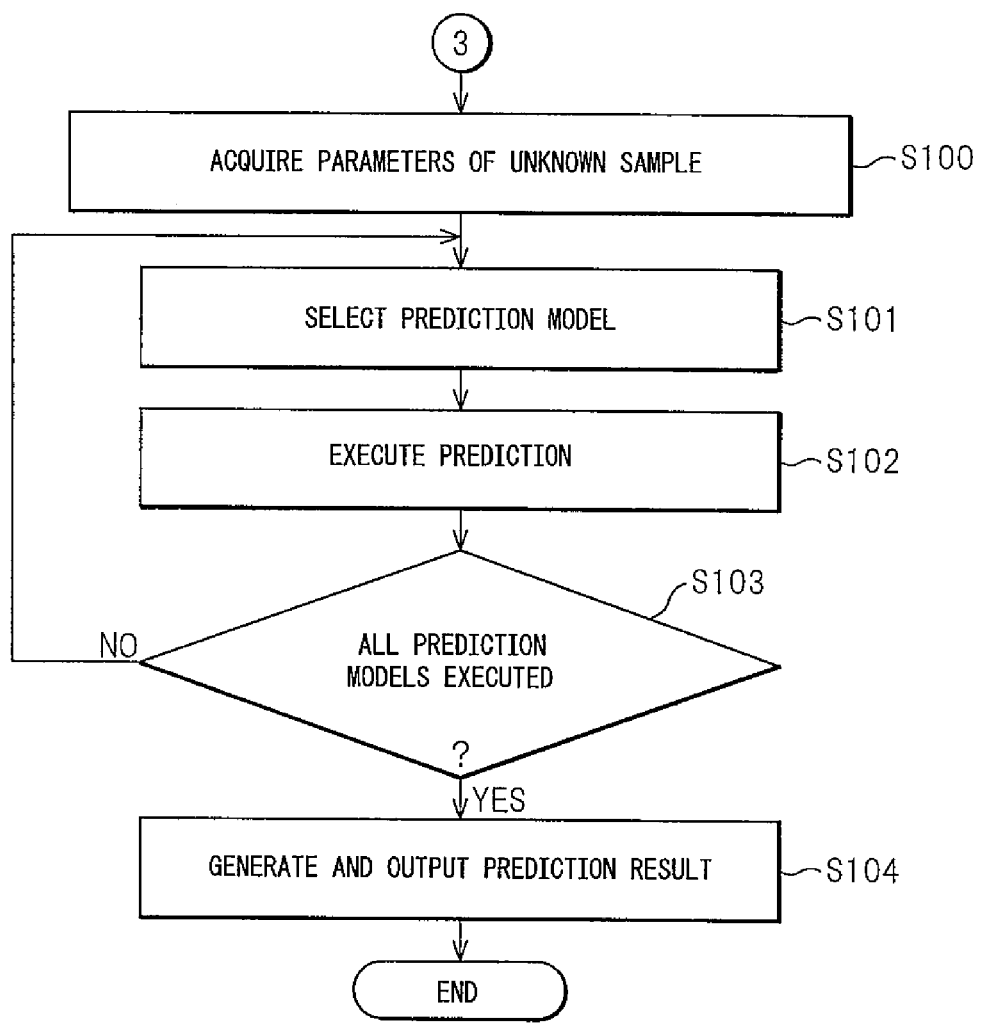
FIG. 10 is a flowchart illustrating the sequence of operations performed within a property prediction value calculation device and an output device in the system of FIG. 3.

FIG. 10 is a flowchart illustrating the sequence of operations performed within the property prediction value calculation device 24 and output device 26 illustrated in FIG. 3. In step S100, the parameter values of the unknown sample are acquired by referring to the unknown-sample parameter generating device 14. In step S101, the prediction model to be executed is selected by referring to the prediction model construction device 22, and in step S102, the prediction values are calculated by applying the parameter values acquired in step S100 to the thus selected prediction model.

In step S103, it is determined whether all of the prediction models listed in the prediction model construction device 22 have been executed or not; if there is any prediction model not yet executed (NO in step S103), the process returns to step S101 to repeat the above cycle of operations. If it is determined in step S103 that all of the prediction models have been executed (YES in step S103), then in step S104 the prediction result is generated and output via the output device 26. In this way, the property prediction of the unknown sample is performed in the system illustrated in FIG. 3.

FIG. 11 illustrates the results of the experiment conducted using the system illustrated in FIG. 3. In the figure, reference numeral 71 indicates ID of unknown sample, and 72 known safety data concerning the unknown sample (in the illustrated example, fish toxicity (LC50: 50% lethal concentration) of the sample). In safety data 72, "1" indicates that the sample has fish toxicity, and "0" indicates that it does not have fish toxicity. Column 73 illustrates the prediction value (value of dependent variable) according to the prior art technique that used AdaBoost as the data analysis method, and column 74 illustrates the prediction value (value of dependent variable) according to the technique of the present invention that used the same data analysis method. In column 74, the symbol "--" indicates that the prediction experiment was not conducted on the corresponding sample.

When attention is paid to the sample of the sample ID 178, it is known that this sample does not have fish toxicity (safety data in column 72 is "0"), but according to the prediction by the prior art technique (column 73) the sample was predicted to have fish toxicity ("1"). On the other hand, according to the method of the present invention (column 74), the sample was correctly predicted to have no fish toxicity ("0"). Further, the sample of the sample ID 189, which is known to have fish toxicity ("1"), was predicted to have no fish toxicity ("0") according to the prediction by the prior art technique. On the other hand, according to the method of the present invention, the sample was correctly predicted to have fish toxicity ("1").

As far as the experiment conducted here is concerned, the presence or absence of fish toxicity in each sample, with the exception of the sample of the sample ID 175, has been correctly predicted by the method of the present invention. This illustrates that the prediction method of the present invention achieves significant improvements in the prediction of unknown samples, and it is therefore presumed that the method of the invention can achieve high prediction rates. The sample of the sample ID 175 has been misclassified as having no toxicity by the technique of the present invention as well as by the prior art technique. This illustrates that investigation from a different perspective is needed which may involve, for example, performing a different data analysis technique and checking its result or performing reexamination of the safety data of that sample.

The conditions and procedure for the experiment of FIG. 11 will be described below. Normally, the property prediction of an unknown sample may be performed on a sample whose safety data is not available, but in that case, it would be difficult to verify the correctness of the prediction. Accordingly, the prediction rate of a prediction system or prediction method is usually calculated by regarding samples with known safety data as unknown samples. In the experimental example of FIG. 11, one sample, for example, the sample of ID 178, was taken as an unknown sample from among 791 training samples registered in the training sample library, and a sub-sample set was constructed based on the remaining 790 training samples; then, a prediction model was generated from this sub-sample set, and the property (safety data) of the sample of ID 178 was predicted using this prediction model. For each of the other samples, the property prediction was performed by selecting an unknown sample and constructing a sub-sample set in the same manner.

In the prior art technique, when the sample of ID 178 was selected as an unknown sample, for example, the prediction value was calculated by constructing a prediction model using all the remaining 790 training samples. By contrast, according to the technique of the present invention, 493 similar samples were extracted from the 790 samples by similarity screening, and the prediction model was constructed using the extracted samples. The number of parameters used for the construction of the prediction model was 65 in both the prior art technique and the technique of the present invention, and both approaches satisfy the data analysis reliability requirements. In the above experiment, the prior art technique failed to produce correct prediction results for a couple of samples, but the technique of the present invention was able to produce correct prediction results.

Each of the above programs can be stored on a computer-readable recording medium, and such recording media can be distributed and circulated for use. Further, each of the above programs can be distributed and circulated through communication networks, such as the Internet. The computer-readable recording media include magnetic recording devices, optical disks, magneto-optical disks, or semiconductor memories (such as RAM and ROM). Examples of magnetic recording devices include hard disk drives (HDDs), flexible disks (FDs), magnetic tapes (MTs), etc. Examples of optical disks include DVDs (Digital Versatile Discs), DVD-RAMS, CD-ROMs, CR-RWs, etc. Example of magneto-optical disks include MOs (Magneto-Optical discs).

INDUSTRIAL APPLICABILITY

The present invention is extensively used to predict the physical and chemical properties of compounds. Its effect is particularly pronounced when the invention is used to predict the safety (toxicity) of compounds which require high prediction accuracy. The safety of compounds concerns biotoxicity in the field of pharmaceuticals, etc., and biotoxicity that becomes a problem in the field of environment, etc., and the safety tests include various toxicity tests and test items such as LC50 (50% lethal concentration) tests, acute toxicity tests, long-term toxicity tests, bioaccumulative tests, biodegradability tests, Ames tests, carcinogenicity tests, chromosome aberration tests, and skin sensitization tests.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention has (have) been described in detail, it should be understood that the various changes, substitutions, and alterations could be made hereto without departing from the spirit and scope of the invention.

What is claimed is:

1. A compound property prediction apparatus comprising:
    a memory storing a training sample library in which a parameter value relating to a chemical structure and a value of a prediction item are preregistered for each individual one of a plurality of training samples;
    an input device which takes data concerning an unknown sample as input;
    a processor, coupled to said memory and said input device, programmed to
        calculate a parameter value of said unknown sample, based on said input data; and, based on said parameter value, calculate a degree of similarity between said unknown sample and individual training samples;
        construct a sub-sample set by extracting training samples whose degree of similarity to said unknown sample is not smaller than a threshold that starts at a predetermined value and is reduced as necessary to ensure that a predetermined minimum number of the training samples are included in the sub-sample set;
        construct a prediction model by performing data analysis on said sub-sample set; and
        calculate a prediction value for said prediction item by applying the prediction model to said unknown sample.

2. The apparatus according to claim 1, wherein said processor determines the degree of similarity between said unknown sample and said individual one training sample by calculating a Tanimoto coefficient based on whether a predetermined partial structure and a predetermined functional group are found in both of said samples.

3. The apparatus according to claim 1, wherein said processor performs cluster analysis on the training samples contained in said training sample library, including said unknown sample, and determines the degree of similarity between said unknown sample and said individual one training sample based on a distance between a cluster containing said unknown sample and a cluster containing said individual one training sample.

4. The apparatus according to claim 1, wherein said processor determines the degree of similarity between said unknown sample and said individual one training sample based on the value of at least one predetermined parameter.

5. The apparatus according to claim 1, wherein said prediction item is safety of a compound.

6. A compound property prediction method comprising:
    acquiring values of a plurality of parameters for an unknown sample of a chemical compound;
    acquiring values of said plurality of parameters for each individual one of training samples of chemical compounds;
    based on values of said plurality of parameters, calculating a degree of similarity between said unknown sample and individual training samples;
    constructing a sub-sample set by extracting training samples whose degree of similarity to said unknown sample is not smaller than a threshold that starts at a predetermined value and is reduced as necessary to ensure that a predetermined minimum number of the training samples are included in the sub-sample set;
    constructing a prediction model by performing data analysis on said sub-sample set; and
    calculating a prediction item representing at least one physical property of the chemical compound by applying said constructed prediction model to said unknown sample.

7. The method according to claim 6, wherein said degree of similarity is determined by calculating a Tanimoto coefficient based on whether a predetermined partial structure and a predetermined functional group are found in both said unknown sample and said individual one training sample.

8. The method according to claim 6, wherein said degree of similarity is determined by performing cluster analysis on said training samples, including said unknown sample, and by detecting a distance between a cluster containing said unknown sample and a cluster containing said individual one training sample.

9. The method according to claim 6, wherein said degree of similarity is determined based on the value of at least one predetermined parameter.

10. The method according to claim 6, wherein said prediction item is safety of a compound.

11. The method according to claim 6, further comprising calculating the degree of similarity between said unknown sample and another unknown sample and, based on a result of said calculation, constructing a sample group containing samples similar to said unknown sample, and wherein
    said prediction item calculating acquires a prediction result by applying said prediction model to each individual sample contained in said similar sample group.

12. A computer readable medium having a program recorded thereon, said program predicting a property of a compound by causing a computer to perform a process comprising:
    acquiring values of a plurality of parameters for an unknown sample;
    acquiring values of said plurality of parameters for each individual one of training samples;
    based on the values of said plurality of parameters, calculating the degree of similarity between said unknown sample and said individual one training sample;
    constructing a sub-sample set by extracting training samples whose degree of similarity to said unknown sample is not smaller than a threshold that starts at a predetermined value and is reduced as necessary to ensure that a predetermined minimum number of the training samples are included in the sub-sample set;

constructing a prediction model by performing data analysis on said sub-sample set; and calculating a prediction item by applying said constructed prediction model to said unknown sample.

13. The medium according to claim 12, wherein said degree of similarity is determined by calculating a Tanimoto coefficient based on whether a predetermined partial structure and a predetermined functional group are found in both said unknown sample and said individual one training sample.

14. The medium according to claim 12, wherein said degree of similarity is determined by performing cluster analysis on said training samples, including said unknown sample, and by detecting a distance between a cluster containing said unknown sample and a cluster containing said individual one training sample.

15. The medium according to claim 12, wherein said degree of similarity is determined based on the value of at least one predetermined parameter.

16. The medium according to claim 12, wherein said prediction item is safety of a compound.

17. The medium according to claim 12, wherein said process further comprising calculating the degree of similarity between said unknown sample and another unknown sample and, based on a result of said calculation, constructing a sample group containing samples similar to said unknown sample, and wherein said prediction item calculating step acquires a prediction result by applying said prediction model to each individual sample contained in said similar sample group.

* * * * *